United States Patent [19]

Leichnitz

[11] 4,329,153

[45] May 11, 1982

[54] TEST TUBE CONSTRUCTION AND METHOD FOR TESTING FOR COPPER AEROSOLS

[75] Inventor: Kurt Leichnitz, Gross-Grönau, Fed. Rep. of Germany

[73] Assignee: Drägerwerk Aktiengesellschaft, Fed. Rep. of Germany

[21] Appl. No.: 192,551

[22] Filed: Sep. 30, 1980

[30] Foreign Application Priority Data

Oct. 23, 1979 [DE] Fed. Rep. of Germany ....... 2942673

[51] Int. Cl.³ .................... G01N 21/78; G01N 31/22
[52] U.S. Cl. .................................. 23/232 R; 422/60; 422/61; 422/86
[58] Field of Search .................. 422/55, 58, 59, 60, 422/61, 83, 86, 87, 88; 23/232 R

[56] References Cited

U.S. PATENT DOCUMENTS

| | | | |
|---|---|---|---|
| 2,908,555 | 10/1959 | Grosskopf | 422/86 |
| 3,022,141 | 2/1962 | Grosskopf | 422/60 |
| 3,985,017 | 10/1976 | Goldsmith | 23/232 R X |
| 4,271,125 | 6/1981 | Leichnitz | 422/60 X |
| 4,272,479 | 6/1981 | Huneke et al. | 422/86 X |

OTHER PUBLICATIONS

*The Merck Index of Chemicals and Drugs*—Seventh Edition, Merck & Co., N.J., 1960, p. 950.

*Primary Examiner*—Arnold Turk
*Attorney, Agent, or Firm*—McGlew and Tuttle

[57] ABSTRACT

An apparatus for testing copper concentration of a test gas comprises a glass tube having breakoff points at each end with an ampoule filled with a nitric acid arranged upstream of a filter which is followed downstream by a reaction layer of silica gel impregnated with a reagent for copper. The glass tube is opened by breaking off breakoff points at each end and the gas to be tested is pumped through the tube so that any suspended particles including copper particles will be deposited on the filter layer too. Thereafter, the ampoule within the glass tube is broken to release the nitric acid which is directed through the filter layer to the reaction layer. The nitric acid which reacts with the copper deposited on the filter layer moves to the reaction layer and produces a discoloration which is proportional to the amount of copper filtered out from the test air. A chart is made up to provide a color standard which is proportional to the copper concentration in the test gas and the discoloration produced in the reaction layer is compared with this color standard to determine the quantity of copper.

8 Claims, 1 Drawing Figure

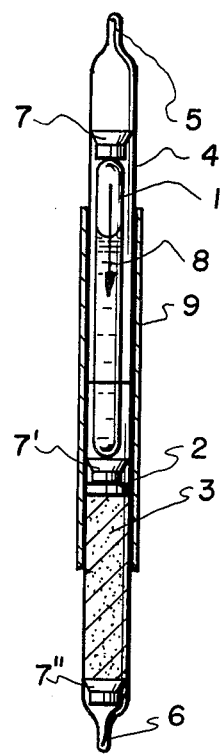

TEST TUBE CONSTRUCTION AND METHOD FOR TESTING FOR COPPER AEROSOLS

FIELD AND BACKGROUND OF THE INVENTION

This invention relates to testing apparatus in general and, in particular, to a new and useful apparatus and method for testing for copper aerosols in a gas, such as air.

The admissible low limiting value of 0.1 mg per m$^3$ for copper fumes at a workplace, according to MAK-value list 1979, indicates the latter to be a potential hazard. Frequent and regular monitoring of these substances in the air is therefore absolutely necessary to avoid health hazards.

A method for determining copper aerosols used for sampling a cellulose diaphragm filter through which the air to be tested is sucked by means of a pump is known. The organic filter material is subsequently dissolved in concentrated heated nitric acid. To dissolve the copper components, the solution which is obtained is then mixed with hydrochloric acid and heated to a high temperature of about 400° C. After cooling, the copper is determined in the oxidizing acetylene-air flame of an atomic absorption spectrophotometer.

A disadvantage of this known method is that it requires a great number of instruments and qualified personnel for carrying out the method, which is cumbersome and time-consuming. In addition, the measuring results are not readily available at the place of sampling (See NIOSH, Manual of Analytical Methods, Sec. Ed. Vol. 3, pg. 186).

SUMMARY OF THE INVENTION

The present invention permits the simple measurement of copper aerosols, which can be effected without great preparation and without loss of time even by less qualified personnel, with the result being immediately available at the place of measurement.

In accordance with the invention, a testing tube is provided which includes an ampoule full of nitric acid arranged upstream of a filter and a reaction layer in that order, and air to be tested is passed through the tube after breaking off breakoff points at each end and any copper particles are deposited in the filter. Subsequently, when the ampoule of nitric acid is broken, the nitric acid will pass through the filter, react with the copper and produce a discoloration in the reaction layer which is proportional to the quantity of copper present in the gas.

The solution of the invention advantageously utilizes the testing tube method. All necessary elements are combined in the testing tube in a consumption unit. The testing tube method is generally known and permits the analyzing of the air for monitoring the workplace in a simple manner. The measuring result is immediately available at the place of measurement. To obtain the measurement, it is only necessary, in a first operation, to open the testing tube points and then to pump the test gas through the testing tube with a known suction pump. In an immediately following second operation, the ampoule is broken and its contents are directed against the reaction layer. In the presence of copper aerosols, the reaction layer is discolored. The intensity of the discoloration is proportional to the mass of copper deposited on the filter layer. Concentrations in the range of 0.05 to 1 mg copper per mu m can be determined.

Accordingly, an object of the present invention is to provide a testing device, which comprises a testing tube made of glass, having breakoff points at each end thereof with an ampoule located in the glass tube containing a nitric acid disposed ahead of a filter layer, and a reaction layer, comprising, a silica gel impregnated with a reagent for copper, the tube being openable at each end so that the gas to be tested may be passed therethrough so that the particles thereof are entrained on the filter and the nitric acid ampoule being breakable to cause the nitric acid to pass through the filter and produce a reaction with the copper which shows up by a discoloration of the material of the reaction layer.

A further object of the invention is to provide a method of testing for copper aerosols which comprises directing the air to be tested through a filter to entrain copper particles, directing a nitric acid into the filter to remove the copper particles to react therewith, and directing the reactants into a reaction layer of silica gel impregnated with a reagent for copper so as to produce a color reaction to determine the copper quantity present in the air.

Another object of the present invention is to provide a testing tube for measuring copper aerosols which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the drawing:

The only FIGURE of the drawing is a sectional view through a testing tube construced in accordance with the present invention.

DESCRIPTION OF THE PREFERRED EMBODIMENT

Referring to the drawing in particular, the invention embodied therein, comprises, an apparatus for testing for copper aerosols which includes a glass testing tube 4, having breakoff points 5 and 6 at respective ends thereof which may be broken off to open the tube for the flow through of a gas to be tested. Within the glass tube 4, there is arranged a breakable ampoule of nitric acid 1, a filter layer 2 and a reaction layer 3, all disposed in successive arrangement, in a direction of the flow 8, held in position by a stopper element 7, 7' and 7''.

Testing tubes for the measurement of a number of gases are known and, consequently, fully developed parts are used. These are the glass tube 4, with the two breakoff points 5 and 6. Filling material 3 in the glass tube 4 and the ampoule 1 are kept shakeproof in the provided sections by holders 7, 7' and 7''. The materials in the tube 4, in the direction of flow 8, successively comprise a breakable ampoule 1, filled with nitric acid, a filter layer 2, and a reaction layer 3 of silica gel, impregnated with a color reagent for copper, e.g., sodium diethyldithiocarbamate. The filter layer may comprise glass cloth or asbestos filter paper. Glass tube 4 is covered in a known manner with a shrunk-on hose 9 at the level of ampoule 1, and it seals glass tube 4 even after its breaking.

The measurement is effected in two operations:

1. After points 5 and 6 have been broken off, the testing tube is placed into a known suction pump, and the gas to be tested is pumped through the testing tube with 100 strokes in the direction of flow 8. The suspended particles, and thus also the copper particles contained in the test gas are deposited in the filter layer 2; and 2. Along with the glass tube 4, ampoule 1 is also broken in the longitudinal axis. The nitric acid is directed from ampoule 1 through filter layer 2 to reaction layer 3 and the color reaction takes place there. The intensity of the discoloration of reaction layer 3 is proportional to the amount of copper filtered out from the test air.

A comparison with an enclosed color standard shows the copper concentration to be determined in the test gas.

While a specific embodiment of the invention has been shown and described in detail to illustrate the application of the principles of the invention, it will be understood that the invention may be embodied otherwise without departing from such principles.

What is claimed is:

1. A test tube for measuring copper aerosols, comprising, a glass tube having breakoff points at each end, a breakable ampoule located within said glass tube, a filter layer arranged downstream of said ampoule, and a reaction layer arranged downstream of said filter layer, means holding said ampoule filter layer and said reaction layer within said tube in order in the flow direction through the tube, the tube being breakable at said breakable points to permit flow of air to be tested therethrough so that the particles thereof become entrained on the filter layer and the ampoule being filled with a nitric acid which, when the ampoule is broken, will flow through the filter layer to produce a reaction with the copper particles and then into the reaction layer, said reaction layer comprising a silica gel impregnated with a color reagent for copper for indicating the presence of copper.

2. A test tube for measuring copper aerosols, as claimed in claimed 1, wherein the color reagent for copper is sodium diethyldithiocarbamate.

3. A test tube for measuring copper aerosols, as claimed in claim 1, wherein said color reagent for copper comprises 4-amino-N, N-dimethyl-aniline sulfate.

4. A test tube for measuring copper aerosols, as claimed in claim 1, wherein said filter layer comprises a glass cloth.

5. A test tube for measuring copper aerosols, as claimed in claim 1, wherein said filter layer comprises asbestos filter paper.

6. A method of testing for copper aerosols in a gas, using a glass testing tube which has ends which may be opened and with a sealed ampoule of nitric acid therein arranged ahead of a filter and a reaction layer in respect to the flow direction, comprising, directing air to be tested through the glass tube after the ends thereof are broken off to cause any copper particles to be entrained in the filter layer, then breaking the ampoule to cause nitric acid to flow into the filter layer and react with the copper particles and then to flow into the reaction layer, and then comparing the color of the reaction layer to obtain an indication of the quantity of the copper therein.

7. A method of testing for copper aerosols in a gas, as claimed in claim 6, wherein said reaction layer comprises a silica gel impregnated with a reagent for copper.

8. A method of testing for copper aerosols in a gas, as claimed in claim 6, including forming a chart with color characteristics comparable to the discoloration of the reaction layer with selected quantities of copper present so as to produce an indicator for comparing a test discoloration with the color of the chart to obtain the quantity of copper present in the air.

* * * * *